US 6,725,079 B2

(12) United States Patent
Zuk et al.

(10) Patent No.: US 6,725,079 B2
(45) Date of Patent: Apr. 20, 2004

(54) DUAL POINTER DEVICE AND METHOD FOR SURGICAL NAVIGATION

(75) Inventors: Yuval Zuk, Haifa (IL); Ehud Katznelson, Ramat-Yishai (IL)

(73) Assignee: Odin Medical Technologies, Ltd., Yokneam Elit (IL)

( * ) Notice: Subject to any disclaimer, the term of this patent is extended or adjusted under 35 U.S.C. 154(b) by 0 days.

(21) Appl. No.: 09/884,097

(22) Filed: Jun. 20, 2001

(65) Prior Publication Data

US 2002/0198448 A1 Dec. 26, 2002

(51) Int. Cl.⁷ .................................................. A61B 5/05
(52) U.S. Cl. ...................................................... 600/414
(58) Field of Search ................................ 600/424, 414, 600/426; 324/318

(56) References Cited

U.S. PATENT DOCUMENTS 6,026,315 A * 2/2000 Lenz et al. .................. 600/414
6,246,896 B1 * 6/2001 Dumoulin et al. ........... 600/411
6,289,233 B1 * 9/2001 Dumoulin et al. ........... 600/410
6,445,943 B1 * 9/2002 Ferre et al. .................. 600/424

* cited by examiner

Primary Examiner—Francis J. Jaworski
Assistant Examiner—Ruby Jain
(74) Attorney, Agent, or Firm—Eitan, Pearl, Latzer & Cohen Zedek, LLP

(57) ABSTRACT

A dual pointing device to be used in cooperation with an imaging apparatus, a tracking system, and an object to be imaged. The dual pointing device provides a means for tracking a point on in image in both the image's frame of reference and Euclidean absolute coordinates. This is accomplished by having two tracking systems follow the dual pointing device. Since the two tracking systems follow the same physical device, and since one tracking system operates in the image coordinates while the other tracking system operates in the absolute coordinates, the device makes it possible to effect automatic transformations between the two systems. More specifically, in the preferred embodiment of the dual pointing device, which is intended for use with a magnetic resonance imager, the absolute tracking system is based on infra-red reflectors on the device that are tracked by an infrared transponder. The image-relative tracking system is based on magnetic resonance responsive samples that are detected by the imager.

25 Claims, 8 Drawing Sheets

DUAL POINTER DEVICE AND METHOD FOR SURGICAL NAVIGATION

FIELD OF THE INVENTION

The present invention relates to magnetic resonance imaging. More particularly it relates to a device and method for determining the position, direction, and/or rotational angle of a pointing device used with an imaging system and in particular with a magnetic resonance imaging apparatus.

BACKGROUND OF THE INVENTION

When performing a medical scanning procedure, precision in localization of different objects or areas within the patient's tissue is of crucial importance. This is especially true for surgical procedures performed in a closed body area, when visualization of the target is impossible (i.e. within the patient's head, stomach etc.). One example is brain surgery, where knowledge of the exact localization of various anatomies allows planning of the procedure and avoiding unnecessary damage to healthy surrounding tissue. Recent diagnostic methods such as computerized tomography (CT), magnetic resonance imaging (MRI), positron emission tomography (PET), nuclear medical apparatus and other medical scanning methods allow accurate pre-operative diagnosis. Nevertheless, these pre-operative pictures are of limited relevance once a surgical procedure is performed since they depend on the coordinates of the patient, which might change during the course of operation due to reasons such as a shift in the patient's position.

To overcome this problem, stereotactic surgery and navigation are commonly used and are based on pre-operative images and on rigid markers fixed to the patient. Still, registration of the patient is always needed to compare pre-operative scans and the current situation during surgery. Moreover, any changes occurring during surgery are not accounted for.

Registration of the patient as a reference for determining the position of surgical instruments or probes is known.

In U.S. Pat. No. 5,782,765 (Jonkman), titled MEDICAL POSITIONING SYSTEM, filed in 1996, and incorporated herein by reference, there was disclosed a method and apparatus for positioning a probe inside a patient including a plurality of transmitter/receiver nodes arranged around the patient for communicating with the probe and generating navigation signals, a system for generating one or more positional signals in response to the navigational signals, and a system for collecting and analyzing those positional signals to determine the location of the medical instrument inside the patient's body. The transmitting/receiving nodes may be arranged on a flexible blanket which is wrapped around and adhered to the patient's body or over a table supporting the patient's body.

U.S. Pat. No. 5,871,455 (Bucholz), entitled SYSTEM FOR INDICATING THE POSITION OF A SURGICAL PROBE WITHIN A HEAD ON AN IMAGE OF THE HEAD, filed in 1995, suggested a similar approach. There was disclosed a system for determining a position of a probe relative to an object such as a head of a body of a patient. The head includes a surface such as a forehead having a contour. Cross sectional images of the head are scanned and stored as a function of the forehead contour. If the forehead contour does not appear in the scan images, then the position of the forehead contour relative to the scan images is determined with an optical scanner and a ring. During surgery, the optical scanner also determines the position of the forehead relative to the ring. An array for receiving radiation emitted from the probe and from the ring generates signals indicating the position of the tip of the probe relative to the ring. A stereotactic imaging system generates and displays an image of the head corresponding to the measured position of the tip of the probe. The system may also display scan images from different scanning technologies which scan images correspond to the same position in the head (See also U.S. Pat. No. 5,383,454).

In U.S. patent application Ser. No. 09/545,383 (Katznelson, et al), entitled SYSTEM AND METHOD OF INTERACTIVE POSITIONING, filed Apr. 7, 2000 and incorporated herein by reference, there was disclosed a positioning system for determining the relation between a coordinate set of a scanning apparatus and a coordinate set of a tracking system so as to allow determining the position of a selected target on an image of a patient acquired by the scanning apparatus in the coordinate set of the tracking apparatus and vice versa, the system comprising:

Reference point means positioned in predetermined location relative to the coordinate set of the scanning apparatus;

Tracking means adapted to detect and determine the position of said reference points means, relative to the coordinate set of the tracking means;

Processing means adapted to communicate with said tracking means and adapted to determine the relation between the coordinate set of the scanning apparatus and the coordinate set of the tracking means, and adapted to translate the coordinates of the target on the image acquired by the scanning apparatus to corresponding coordinates on the coordinate set of the tracking means.

However, there are several sources of distortion that affect the accuracy of translation of the coordinate set of the tracking means to the target on the image acquired by the scanning apparatus, which is assumed here to be a magnetic resonance imaging (MRI) device.

First of all, distortion can occur due to the difference between the geometry of the tracking system and that of the image.

The tracking coordinates are Euclidian (having three orthogonal axes where the unit of measurement is constant) whereas the image is only approximately Euclidean. Mapping between the two becomes increasingly inaccurate as the tracking device (pointer) is moved away from the center of the image volume. This inaccuracy can be globally corrected by measuring the magnetic field and the gradient field. However for greater accuracy, local corrections are required. For example, when moving to a given point on an imaged object, increasingly local corrections are required as the pointer moves in absolute space closer and closer to the target on the image.

It is therefore desirable that there be a means for generating local corrections for any subvolume of the imaging volume.

Another limitation of the correction is that it becomes invalid if there are changes in environmental factors over time. Such factors include the effect of movement of ferromagnetic devices and of changes in temperature.

Each time that such an environmental change occurs, it can cause a change in the distortion in the image and therefore a new correction must be generated. It is sometimes inconvenient or even impossible to generate new corrections each time such an environmental change creates the need for one. For example, when MRI is used during surgery, the patient would have to be moved so that the correction could be generated.

Therefore it is also desirable that there be a way to easily correct for discrepancies in the mapping of the tracked point to the image.

The incorporation of magnetic resonance imaging (MRI) techniques in surgical procedures is known for some years now. Interventional MRI (iMRI), also referred to as intra-operative MRI, allows surgeons to obtain a practically real time image of the patient's body part under surgery and to receive immediate feedback on the outcome of the operation carried out.

Israel Pat. Appl. No. 119558 (Katznelson et al.) filed Nov. 4, 1996, incorporated herein by reference, discloses a compact, transportable, intra-operative MRI System, which includes a host computer coupled to a central electronics system which may be coupled to different MRI probes.

Compact MRI systems for performing local imaging of specific body parts or organs may use a hollow tube-like magnet assembly or other assemblies, such as two opposing magnets, such as described in U.S. Pat. No. 5,900,793 (Katznelson et al.), filed Jul. 23, 1997 incorporated herein by reference.

U.S. Pat. No. 5,735,278 (Hoult et al.), filed Mar. 15, 1996, disclosed an apparatus for use in surgical procedure comprising an operating table for receiving a patient for surgery and an MRI system for obtaining images of a part of the patient as a series of time through the surgical procedure for analysis by the surgical team to allow monitoring the progress of the surgery. The high field magnet and the operating table are shaped and arranged for positioning of the part of the patient into the magnetic field while the patient remains in place on the table and the magnet is mounted for movement between a first position spaced from the table and the patient thereon to allow the surgical team to carry out the surgical procedure and a second position for applying the magnetic field to the part of the patient. The table remains substantially stationary and only the magnet is moved to a position spaced from an adjacent end of the table to allow the surgical team to move around the adjacent end of table and to each side of the table to access the patient.

Usually an interventional MRI system (iMRI), such as the ones discussed above, would comprise an MRI system, with a magnet, positioned over an operating table. The magnet assembly is constructed so as to leave open spaces around the patient allowing the medical team to attend the patient. Another solution was the introduction of a magnet probe that can be brought near the patient lying on the operating table to perform the imaging, and then retracted to clear the way for the medical staff to access the patient.

MRI in particularly is appealing for its outstanding ability of obtaining contrast images, differentiating between different tissue types and allowing the visualization and detection of pathologies.

When performing brain surgery to remove a brain tumor it is desirable not to remove healthy tissue together with the tumor. Any unnecessary removal of brain tissue may result in serious repercussions inflicting substantial neurological damage. For this reason surgeons are usually capable of removing only a large portion of the tumor, leaving some residual malignant tissue. MRI provides the medical staff with good contrast images that allow the surgeons to locate malignant tissue and evaluate its dimensions.

A major difficulty encountered during a tumor removal procedure is related to the fact that although it is possible to perform known MRI sequences in order to acquire good contrast MRI images thus allowing differentiation between malignant and healthy tissue on the image acquired, it may not be possible to notice the difference on the operated tissue itself. The surgeon can clearly see the tumor and its boundaries on the image, but is unable to distinguish the tumor from its surrounding healthy tissue in the patient. For that reason, to date, only about as much as 70% of a brain tumor is removed in a conventional brain surgery. This may lead to future aggravation in the patient's condition, as the tumor grows back, seriously affecting the patient's quality of life or even endangering his life.

For that reason it is sought to provide means for aiding the medical staff in determining the exact location of a medical instrument used in operation with reference to the image obtained using MRI apparatus. Furthermore it is desirable that such means enable determining the orientation of such instrument.

In U.S. Pat. No. 5,271,400 (Dumoulin et al.), filed Apr. 1, 1992, there is disclosed a tracking system to monitor the position and orientation of a device using magnetic resonance detection of a sample contained within a device. The detectable device, which can be a guide wire, a catheter, an endoscope, a laparoscope, a biopsy needle or a similar device, contains an RF (radio frequency) coil and a magnetic resonance responsive sample. When the device is subjected to an RF pulse, generated by an outside RF coil or by the RF coil of the device, the MR responsive sample resonates, and the RF coil of the device, which is a small coil, detects the MR response signal from the MR responsive sample. The coordinates of the MR responsive sample are calculated, and its position is marked on the MRI image, so as to enable the beholder to determine the relative position of the device with respect to the conventional image. It is explained that it is a purpose of that invention to provide a method for tracking a device using MR examination without loss of signal due to lack of MR responsive material in the internal cavities of a subject.

In U.S. Pat. No. 5,318,025 (Dumoulin et al.), filed Apr. 1, 1992, there is disclosed a tracking system to monitor the position and orientation of a device using magnetic multi-plexed resonance detection. The detectable device disclosed contains a number of RF coils (instead of just one as described in U.S. Pat. No. 5,271,400). The inventors of U.S. Pat. No. 5,318,025 do not explicitly explain the reason for providing at least two RF coils, but it is understood that this allows determining linear orientation (as only one RF coil is provided in the device described in U.S. Pat. No. 5,271,400). However the tracking device disclosed in U.S. Pat. No. 5,318,025 (having three aligned and evenly spaced RF coils) does not facilitate obtaining information as to the directionality of the device, and that may be determined only by other independently acquired medical diagnostic devices, as is explained there.

U.S. Pat. No. 5,916,162 (Snelten et al.) discloses an invasive device which is intended to cooperate with an MRI apparatus. The device is provided with an RF coil situated near the distal part of the invasive device. The RF coil is used to visualize the position of a distal end of the invasive device, introduced into an object, in an image of the object. In order to counteract the development of heat in the invasive device, the invasive device is provided with a hollow carrier. The electric connection extends through said carrier, which is provided with an electrically conductive shield with an additional resistance. The invasive device disclosed in Snelten's patent is in fact a catheter for insertion into a blood vessel of a patient.

In U.S. patent application Ser. No. 09/545,384 (Livni, et al), entitled MRI POINTING DEVICE AND METHOD FOR DETERMINING POSITION AND ORIENTATION, filed Apr. 7, 2000 and hereby incorporated by reference, there was disclosed a pointing device to be used in cooperation with a magnetic resonance imaging apparatus. The pointing device comprising:

a member of a predetermined shape;
at least one sample of magnetic resonance responsive material placed within said member in a predetermined position, said sample geometrically arranged to have a distinct directionality;
whereby when said device is introduced into said magnetic resonance imaging apparatus image region, the position sample may be obtained and marked on an image of said target.

Two limitations can affect the accuracy of the MRI pointing device.

One limitation occurs when there is a need to track two or more points where the desired distance between the points is greater than the portion of the imaging field occupied by the pointing device.

An example of where this need can arise is when it is necessary to point to a target that lies beyond the tip of the pointing device (for example, a point deeper in the tissue than the pointer's penetration). To point to the target, two points on the pointing device are tracked and the line connecting them is projected to the target. The greater the distance between the two points, the greater the accuracy of the projection.

The MRI imaging volume is relatively limited to begin with and most of it is normally taken up by the object being imaged. Therefore the distance between tracked points on the pointer that can be captured within the MRI imaging volume is relatively small.

The desired state would be for the margin of error of the projection to the target to be smaller than the discretization (image resolution). To accomplish this, it is desirable that there be a way to extend the distance between the tracked points on the pointer, such that at least one endpoint of the projected line could be tracked outside the boundary of the imaging volume.

Another limitation occurs when other devices in the vicinity of the MRI device cause RF interference with the MRI signal. Often the operation of these devices is required, for example during an operation, and therefore they cannot simply be shut off. The RF interference can cause one or more false MRI points to register. Therefore, there is a need to overcome the problem of RF interference.

When dealing with RF interference, a distinction must be made according to whether the interference is constant over time. If it is constant, a rough filter can be generated by following this procedure:

1. Stop transmitting from the MRI device.
2. Try to register the MRI pointer.
3. For each frequency, detect any amplitude that extends beyond the average noise (these are false peaks).
4. Resume transmission from the MRI device
5. Filter out by subtraction the amplitudes detected in step 3.

However it is desirable to have a solution for the case where the RF interference changes over time. Such a solution would provide an independent means for identifying false peaks as they occur.

In summary, it is a main object of the present invention to combine an external tracking means and an image-registered tracking means in a pointer to be used with an imaging apparatus.

It is another main object of the present invention to enable local corrections for mapping an external tracking means to an image as required.

It is another main object of the present invention to enable tracking points both inside and outside an imaging volume.

It is another main object of the present invention to automatically filter any RF interference, including time-dependent interference, which creates false peaks in the projections of an image-registered tracking means.

BRIEF DESCRIPTION OF THE INVENTION

There is thus provided in accordance with a preferred embodiment of the present invention, a dual pointing device to be used in cooperation with an imaging apparatus, a tracking system, and an object to be imaged, the pointing device comprising:

a. a pointing member of a predetermined shape;
b. at least one sample of material responsive to the imaging apparatus, located on or inside said pointing member in a predetermined position and arranged, according to its composition, shape, or geometry, to register as a distinct point in an image acquired by the imaging apparatus;
c. at least one marker registerable on the tracking system, the marker located within said pointing member in a predetermined position and arranged, according to its geometry or other properties, so that the tracking system can determine information about the pointing member such as the location of the pointing member's tip and the pointing member's direction;
d. a processing means adapted to communicate with the tracking system and the imaging apparatus, to determine the relation between the coordinate set of the imaging apparatus and the coordinate set of the tracking means, and to translate the coordinates of said pointing member's tip as determined by the tracking system, from the absolute coordinate set of the tracking means to the coordinate set of the imaging apparatus and to superimpose it on the image;
whereby the location of said pointing member's tip in the image coordinates and its location in the tracking system coordinates are known.

Furthermore, in accordance with another preferred embodiment of the present invention, the imaging apparatus is an an ESR (electron spin resonance) system.

Furthermore, in accordance with another preferred embodiment of the present invention, the imaging apparatus is a gradient tracing system.

Furthermore, in accordance with another preferred embodiment of the present invention, the location of said pointing member's tip in the image coordinates and its location in the tracking system coordinates are superimposed in an image acquired by the magnetic resonance imaging apparatus.

There is thus also provided in accordance with a preferred embodiment of the present invention, a dual pointing device to be used in cooperation with a magnetic resonance imaging apparatus, a tracking system, and an object to be imaged, the pointing device comprising:

a. a pointing member of a predetermined shape;
b. at least one magnetic resonance responsive sample, located on or inside said pointing member in a predetermined position and arranged, according to its composition, shape, or geometry, to register as a distinct point in an image obtained by the magnetic resonance imaging apparatus;
c. at least one marker detectable by the tracking system, the marker located within said pointing member in a predetermined position and arranged, according to its geometry or other properties, so that the tracking system can determine information about the pointing member such as the location of the pointing member's tip and the pointing member's direction;

d. a processing means adapted to communicate with the tracking means and the magnetic resonance imaging apparatus, to determine the relation between the coordinate set of the magnetic resonance imaging apparatus and the coordinate set of the tracking means, and to translate the coordinates of said pointing member's tip as determined by the tracking system, from the absolute coordinate set of the tracking means to the coordinate set of the magnetic resonance imaging apparatus and to superimpose it on an image;

whereby the location of said pointing member's tip in the image coordinates and its location in the tracking system coordinates are superimposed in an image acquired by the magnetic resonance imaging apparatus.

Furthermore, in accordance with another preferred embodiment of the present invention, the magnetic resonance imaging apparatus is an interventional magnetic resonance imaging apparatus, constructed so as to provide medical personnel with access to the patient before, during, and after the imaging.

Furthermore, in accordance with another preferred embodiment of the present invention, the tracking system is based on an infra-red transponder and the markers are infra-red reflective materials.

Furthermore, in accordance with another preferred embodiment of the present invention, the tracking system is based on an infra-red receiver and IR source markers.

Furthermore, in accordance with another preferred embodiment of the present invention, the tracking system is based on an electromagnetic radiation transponder and the markers are electromagnetic-radiation-reflective materials.

Furthermore, in accordance with another preferred embodiment of the present invention, the tracking system is based on a video camera and the markers are are video-detectable materials.

Furthermore, in accordance with another preferred embodiment of the present invention, the tracking system is based on an acoustic transponder and the markers are sound-radiation or sound-reflective materials.

Furthermore, in accordance with another preferred embodiment of the present invention, the pointing member is elongated.

Furthermore, in accordance with another preferred embodiment of the present invention, the pointing member is tube-shaped.

Furthermore, in accordance with another preferred embodiment of the present invention, the pointing member is incorporated in a surgery-room tool.

Furthermore, in accordance with another preferred embodiment of the present invention, the magnetic resonance responsive samples comprise water or gadolinium or nickel chloride solution provided in voids of distinct shape within said member.

Furthermore, in accordance with another preferred embodiment of the present invention, the magnetic resonance responsive samples are provided in the shape of cones.

Furthermore, in accordance with another preferred embodiment of the present invention, the magnetic resonance responsive samples are provided in the shape of discs.

Furthermore, in accordance with another preferred embodiment of the present invention, the magnetic resonance responsive samples are provided in other shapes.

Furthermore, in accordance with another preferred embodiment of the present invention, the magnetic resonance responsive samples are geometrically arranged within said member to have a distinct directionality.

Furthermore, in accordance with another preferred embodiment of the present invention, the magnetic resonance responsive samples are differentiated by MRI contrast.

Furthermore, in accordance with another preferred embodiment of the present invention, the device includes one of said magnetic resonance responsive samples.

Furthermore, in accordance with another preferred embodiment of the present invention, the device includes three of said magnetic resonance responsive samples.

Furthermore, in accordance with another preferred embodiment of the present invention, the three magnetic resonance responsive samples are each provided in a shape of a disc.

Furthermore, in accordance with another preferred embodiment of the present invention, the gaps between said three magnetic resonance responsive samples are distinctly different whereby this aides in determining the directionality of said device.

Furthermore, in accordance with another preferred embodiment of the present invention, the device is further provided with a radio frequency coil in the vicinity of at least one of said magnetic resonance responsive samples, said RF coil adapted to allow it to be electrically connected to said magnetic resonance imaging apparatus.

Furthermore, in accordance with another preferred embodiment of the present invention, said radio frequency coil encircles said sample of magnetic resonance responsive material.

Furthermore, in accordance with another preferred embodiment of the present invention, the radio frequency coil is embedded in said sample.

Furthermore, in accordance with another preferred embodiment of the present invention, said markers are geometrically arranged within said member to have a distinct directionality.

Furthermore, in accordance with another preferred embodiment of the present invention, said markers are geometrically arranged within said member to have a distinct rotational angle.

Furthermore, in accordance with another preferred embodiment of the present invention, the device includes one of said samples.

Furthermore, in accordance with another preferred embodiment of the present invention, the device includes three of said samples.

There is thus also provided in accordance with a preferred embodiment of the present invention, a method for enabling accurate positioning and tracking of an object relative to that object's coordinates in physical space and its coordinates in an image of the object, comprising:

a. providing a tracking means,
b. providing a magnetic resonance imaging means;
c. providing a dual pointing means comprising marking means detectable by said tracking means and magnetic resonance responsive means,
d. providing a processing means;
e. pointing with said dual pointing means in the imaging volume of the magnetic resonance imaging means,
f. tracking the location of said marking means,
g. calculating the direction and tip location of said dual pointing means, based on said tracking by said tracking means;

h. acquiring an image with said magnetic resonance imaging means,
i. applying the same projection sequence used to acquire said image to obtain three projections of the magnetic responsive means,
j. processing said projections to calculate the direction of the dual pointing device and the location of its tip—based on said magnetic responsive means;
k. calculating the magnitude of the mapping error between the location of the dual pointing means's tip according to said tracking means and its location according magnetic resonance responsive means,
l. calculating a local transformation for the mapping error,
m. repeating these steps (a) to (l) to obtain mapping errors for a number of points,
whereby, said local transformations can be applied to accurately map the coordinates of said dual pointing device in physical space as tracked by said tracking means to its coordinates in the image as calculated from the magnetic responsive means.

Furthermore, in accordance with another preferred embodiment of the present invention, the method further comprises displaying the mapping error as well as the location and direction of the dual pointing means, as determined from the tracking means and as determined from the magnetic resonance responsive means, in the image.

Furthermore, in accordance with another preferred embodiment of the present invention, the method further comprises that said magnetic resonance imaging means is an interventional magnetic resonance imaging means.

There is thus also provided in accordance with a preferred embodiment of the present invention, a method for projecting a vector into an image captured by a magnetic resonance imaging means, comprising
a. providing a tracking means,
b. providing a magnetic resonance imaging means;
c. providing a dual pointing means comprising marking means detectable by said tracking means and magnetic resonance responsive means,
d. providing a processing means;
e. pointing with said dual pointing means in the imaging volume of the magnetic resonance imaging means,
f. tracking the location of said marking means,
g. acquiring an image with said magnetic resonance imaging means,
h. applying the same projection sequence used to acquire said image to obtain three projections of said magnetic responsive means,
i. processing said three or six projections to calculate the location of the magnetic responsive means;
j. calculating the vector using as end points the location of the markers and the location of the magnetic resonance responsive means,
k. displaying the vector in the image.
whereby a vector is projected into the image.

Furthermore, in accordance with another preferred embodiment of the present invention, the method further comprises that the margin of error for the vector is smaller than the image discretization.

Furthermore, in accordance with another preferred embodiment of the present invention, the method further comprises that said magnetic resonance imaging means is an interventional magnetic resonance imaging means.

There is thus also provided in accordance with a preferred embodiment of the present invention, a method for filtering out false peaks in the projections of a magnetic resonance signal acquired by a magnetic resonance imaging means, comprising:
a. providing a tracking means,
b. providing a magnetic resonance imaging means;
c. providing a dual pointing means comprising marking means detectable by said tracking means and magnetic resonance responsive means,
d. providing a processing means;
e. pointing with said dual pointing means in the imaging volume of the magnetic resonance imaging means,
f. tracking the location of said marking means,
g. acquiring an image with said magnetic resonance imaging means,
h. applying the same projection sequence used to acquire said image to obtain three projections of said magnetic responsive means,
i. calculating, where there is more than one peak above noise in any projection of the magnetic resonance responsive samples, the distance to the center of gravity, for each possible location of the tip of the dual pointing means indicated by the magnetic resonance responsive samples.
j. disregarding all locations where the calculated distance conflicts with the known distance between said markers and said magnetic resonance responsive means,
k. displaying the tip of the dual pointing means as indicated by the remaining location indicated by the magnetic resonance responsive sample.
whereby radio frequency interference is prevented from interfering with tracking the dual pointing means in the magnetic resonance image.

Furthermore, in accordance with another preferred embodiment of the present invention, the method further comprises that said magnetic resonance imaging means is an interventional magnetic resonance imaging means.

BRIEF DESCRIPTION OF THE FIGURES

The invention is described herein, by way of example only, with reference to the accompanying Figures, in which like components are designated by like reference numerals.

DETAILED DESCRIPTION OF THE INVENTION

Figure 1A:
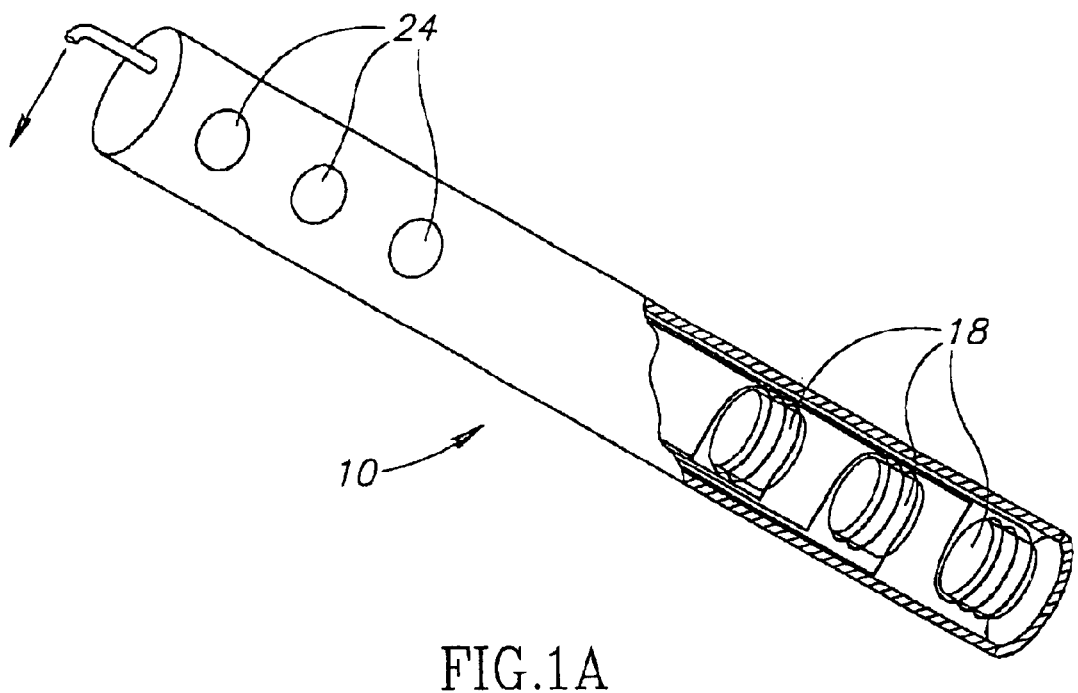
FIG. 1A illustrates a dual pointer in accordance with a preferred embodiment of the present invention, combining infra-red (IR) reflective components for tracking in absolute coordinates and magnetic resonance detectable components for tracking in the image coordinates.

The present invention is a dual pointer for use with an imaging system, more specifically, for use during a medical procedure. A typical use of the dual pointer would be to enable a human or robot surgeon to move an instrument to the precise physical location of a point in a magnetic resonance image. The dual pointer is an elongated object containing two sets of elements.

One set of elements is tracked relative to absolute coordinates. The absolute location of both the dual pointer and the imaging volume are known, therefore the dual pointer location relative to the absolute coordinates can be tracked and superimposed on the image.

The absolute coordinate tracking in the proposed invention is assumed to be based on an optical system that tracks IR (infra-red)-reflective elements on the dual pointer. However another absolute coordinate tracking system could be used, for example an AC (alternating current) tracking system.

The other set of elements on the pointer is detected directly by the imaging device. Since the elements and the image itself are both detected by the same device, the point tracked through these elements is displayed in its exact location relative to the image.

The local (in-image) tracking in the proposed invention is assumed to be carried out using an MRI (magnetic resonance imaging) device to track magnetic resonance responsive elements on the dual pointer. However, the invention could also be implemented using another imaging device, such as an ESR (electron spin resonance) system or a gradient tracing system, with elements responsive to that imaging device used for the purpose described here for the magnetic resonance responsive elements.

The basic premise of the proposed invention is to take object motion (physical movement of pointer), which occurs in the absolute coordinate system, and match it as closely as possible to object description (pointer representation in the image).

To physically bring the pointer to a given point on the image, a transformation between the image coordinate system and the absolute coordinate system is required. In the proposed invention the transformation is automatic: the same pointer registers in both the absolute coordinate system and the image.

It is a main object of the present invention to enable local corrections for deviation from Euclidean mapping of the IR point to the image to be made easily whenever required (including when required due to environmental factors).

The pointer location is always tracked with reference to both the absolute coordinate system and the image coordinate system. Therefore, each time the pointer is moved, a local correction is measured. If enough local corrections are measured in a given volume, local mapping can be determined for that volume.

With local mapping completed, the two points (the absolute-coordinate IR point and the image-coordinate MRI point) will be superimposed on the same point in the in-plane image.

As the pointer is moved out of the local volume, the correction may become invalid. In that case, a gap develops between the IR point and the MRI point in the image.

It is another main object of the present invention to enable measuring points at significant distance from one another. This is possible because the IR reflectors are independent of the imaging device and therefore one or more IR points can be outside the imaging volume.

It is another main object of the present invention to automatically filter any RF (radio-frequency) interference, including time-dependent interference, that creates false peaks. If the RF interference creates a false peak, the pointer detects that the false peak is incompatible with the pointer construction and filters the peak out. For example, RF interference could falsely indicate an MRI point that is further than the MRI point's known distance from the IR point. The system would reject this as a false point.

The system and method of the present invention is hereby described with reference to the accompanying drawings.

Reference is now made to FIG. 1A illustrating a dual pointer in accordance with a preferred embodiment of the present invention.

A dual pointer consisting of a pointer 10, (tube or similar article), contains at or near its tip (distal end) one or more MRI-responsive samples.

The preferred embodiment of the dual pointer shown in FIG. 1A includes three MRI-responsive samples 18 at the distal end (tip) with each sample preferably encircled by an RF coil 12. The RF coils are not essential to the invention but they serve to enhance the MRI signal induced in the samples and received by the imaging antenna. The MRI responsive samples are tracked in the MRI image.

In the preferred embodiment of the present invention, three IR-reflective elements 24 are located at or near the other end (proximal end) of the pointer 10. The IR-reflective elements are tracked by an optical tracking system 40 in absolute coordinates.

FIG. 1A serves to illustrate the fact that both the IR-reflective elements 24 and the MRI responsive samples 18 are on the same physical pointer 10. While three of each set of elements are shown in FIG. 1A, the quantity of each set used can vary depending on factors such as the use to which the dual pointer will be put, whether more than one pointer will be used simultaneously and therefore there is a need to be able to differentiate between dual pointers, and the level of accuracy required. What is germane to the present invention is that there is one or more MRI responsive samples that are detected by the MRI device and one or more IR-reflective elements that are tracked by the optical tracking system.

In this specification, "MRI point" refers to the location of the pointer's tip in the image as based on data from the MRI responsive samples and "IR point" refers to the registration of the pointer's in the image based on data from the IR-reflective elements.

The IR-reflective elements 18 on the pointer are passive reflectors, therefore the differentiation between them is just their relative geometry (not the shapes or other properties of the individual reflectors).

With four IR reflectors, the pointer's rotation around its axis, direction, and tip (by extrapolation) can be tracked. Optionally, more than four IR reflectors can be used for greater accuracy or for differentiating between pointers where more than one is used (i.e., by each pointer having a different number of IR reflectors).

Three IR reflectors can be used. However when only three on a line are used, rotation around the axis cannot be tracked.

Figure 1B:
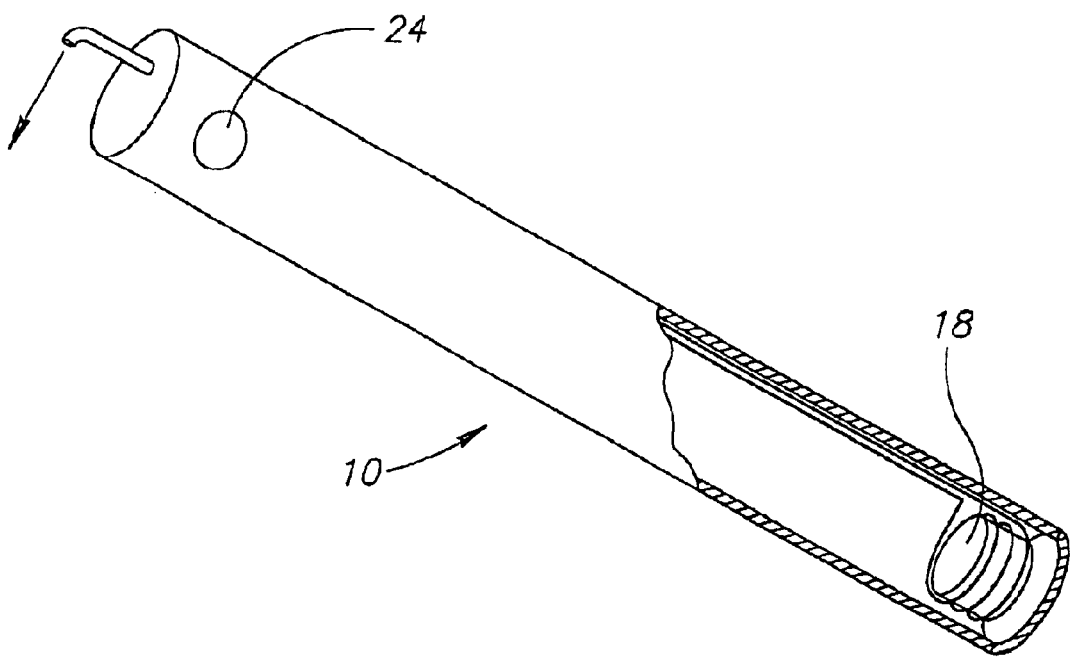
FIG. 1B illustrates a dual pointer in accordance with an alternative embodiment of the present invention, combining a single infra-red (IR) reflective component for tracking in absolute coordinates and a single magnetic resonance detectable component for tracking in the image coordinates.

In an alternative embodiment of the present invention, where the IR reflector is only used for providing a reference point for the MRI point (as described later in this description), then one IR reflector is sufficient. FIG. 1B shows such an embodiment with one IR reflector and one magnetic responsive element.

The magnetic resonance responsive elements can, like the IR reflectors, be differentiated by geometry, but also by the material and shape of the individual elements.

The magnetic resonance responsive elements are primarily used for pointing.

A single magnetic resonance responsive element is adequate to provide a point. For a line, two elements are required, and for a vector, three or more elements or a single elongated element are required.

Figure 2:
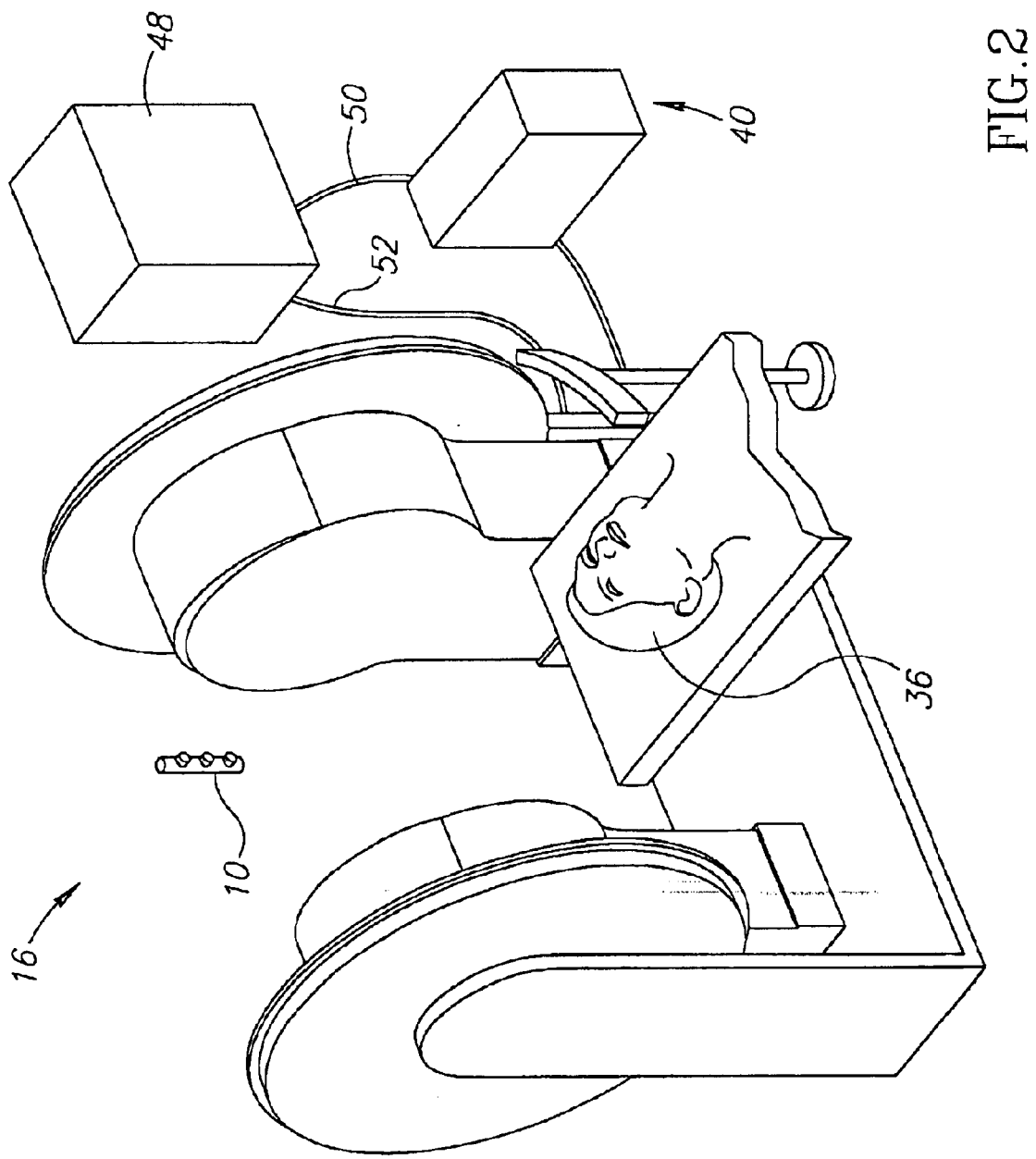
FIG. 2 is a diagram of a dual pointer integrated into a magnetic resonance imaging (MRI) apparatus equipped with an IR tracking system, in accordance with a preferred embodiment of the present invention.

Reference is now made to FIG. 2, illustrating a general view of a dual pointer positioning system in accordance with a preferred embodiment of the present invention.

An MRI device 18 is shown with a patient 36 who will be scanned by the MRI device. Alternatively, an interoperative MRI (iMRI) device can be used.

An IR tracking system 40 is used to register the IR reflectors 24 on the dual pointer 10. Based on the reflector positions and their known geometry, the IR system can determine the dual pointer tip, the dual pointer's direction, and its rotation around its axis.

The IR tracking system communicates (wire 50) with the scanner's processing unit 48. Processing unit 48 is the analyzer and image generator of the MRI apparatus and naturally communicates with the imaging side (i.e. the magnet assembly, the gradient coils, and the RF antenna, not shown in the Figure) of the MRI apparatus via wire 52.

In processing unit 48 (usually a computer) the coordinate sets of the MRI scanner 18 and the IR reflectors 24 are combined and superimposed on the image obtained by the MRI scanner 18. The result is superimposition of a point on the image according to the absolute coordinates of the dual pointer. This point is referred to herein as the IR point. Depending on the geometry and quantity selected for the IR samples 24.

The magnetic resonance responsive samples 18 on the dual pointer are registered by the MRI scanning device, either during the scanning of the volume or during briefer scans intended only to detect the dual pointer. The information about the magnetic resonance responsive samples 18 is sent to the scanner's processing unit 48 where it is analyzed to determine the location of the dual pointer's tip according to the known geometry and properties of the magnetic resonance responsive samples 18 and superimposes the point on the image according to the image coordinates. This point is referred to herein as the MRI point.

The processing unit 48 is also used to carry out the calculations and image manipulation involved in the procedures described below.

It is recommended, in order to maximize the reduction of the error of the registration, to perform initial registration of the IR point using known methods relative to either the imaging apparatus or the patient. However initial registration can also be done using the dual pointer alone as is described later in this specification.

Once registration has been completed, the IR reflectors on the dual pointer are continually tracked by the IR system.

An MRI image is obtained following standard procedure:
1. Placing a patient in imaging region of a MRI apparatus;
2. Applying predetermined imaging sequence, view gradient strength, oblique axes and bandwidth;
3. Processing retrieved MRI data to obtain an image of the patient's imaged part;

The location of the IR point is determined by the IR tracking system based on the location of the IR-reflectors on the dual pointer. As the dual pointer moves, the IR tracking system continuously updates the location of the IR point. The IR point is communicated by the IR tracking system to the processing means, which is adapted to register the IR point on the image.

The MRI point of the dual pointer can be tracked in the following manner (this procedure can be done continuously if desired).
1. Placing the dual pointer containing magnetic resonance responsive material (and IR reflectors) in the imaged volume;
2. Applying a projection sequence having same predetermined view gradient strength, oblique axes and bandwidth as those used to acquire the MRI image;
3. Obtaining six or three projections in the predetermined oblique axes of the pointing device.
4. Processing the projections to determine the MRI point and superimposing it on the image.

The system as described to this point superimposes both an absolute coordinate point (IR-tracked) and image coordinate point (MRI-tracked). Since both IR tracked and MRI-tracked pointers already exist, the primary novelty thus far is the fact that the two are combined on the same physical pointer or tube 10.

Further novelty arises from the procedures that this new combination makes possible, and which overcome the problems mentioned in the Background section of this disclosure. These procedures are described below.

From this point on, the processing unit will normally be superimposing both the MRI point and the IR point on the image and moving the superimposed points to correspond with the movement of the dual pointer (assuming that the MRI point is continuously measured).

Figure 3:
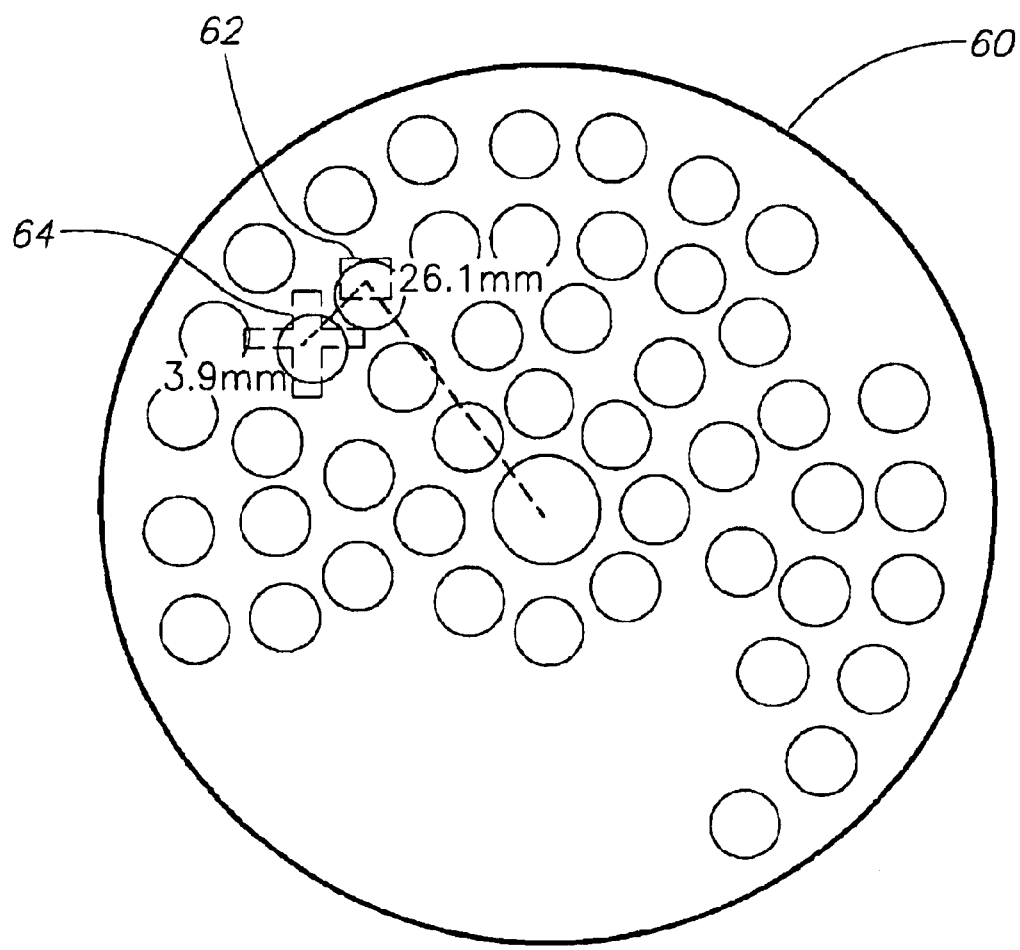
FIG. 3 is a representation of an MRI image showing both an IR-tracked point and an MRI-tracked point, where the mapping of the two points is distorted. This problem is overcome by the present invention.

When the dual pointer is pointing to a point where the registration is correct, the MRI point and the IR point will appear to be in the same location (difference is less than discretization). If the registration is incorrect, the two points will appear in different locations. In the preferred embodiment of the present invention, the processing device is programmed to display the magnitude the error between the points. This is illustrated in FIG. 3, which is an example of an MRI image of a phantom 60, with both the MRI point 62 and the IR point 64 superimposed on the image. The MRI point 62 is highlighted with a box. It is 26.1 mm from the center of the volume. The IR point 64 is highlighted with a cross. It is 3.9 mm from the MRI point 62. The distortion between the MRI point 62 and the IR point 64 indicates that a local transformation is needed. The cause of distortion could be due to incorrect mapping of the IR point (Euclidean coordinates) to the MRI point (non-Euclidean coordinates) or due to changes in the environment (temperature changes, movement of ferromagnetic devices, etc.).

Figure 4:
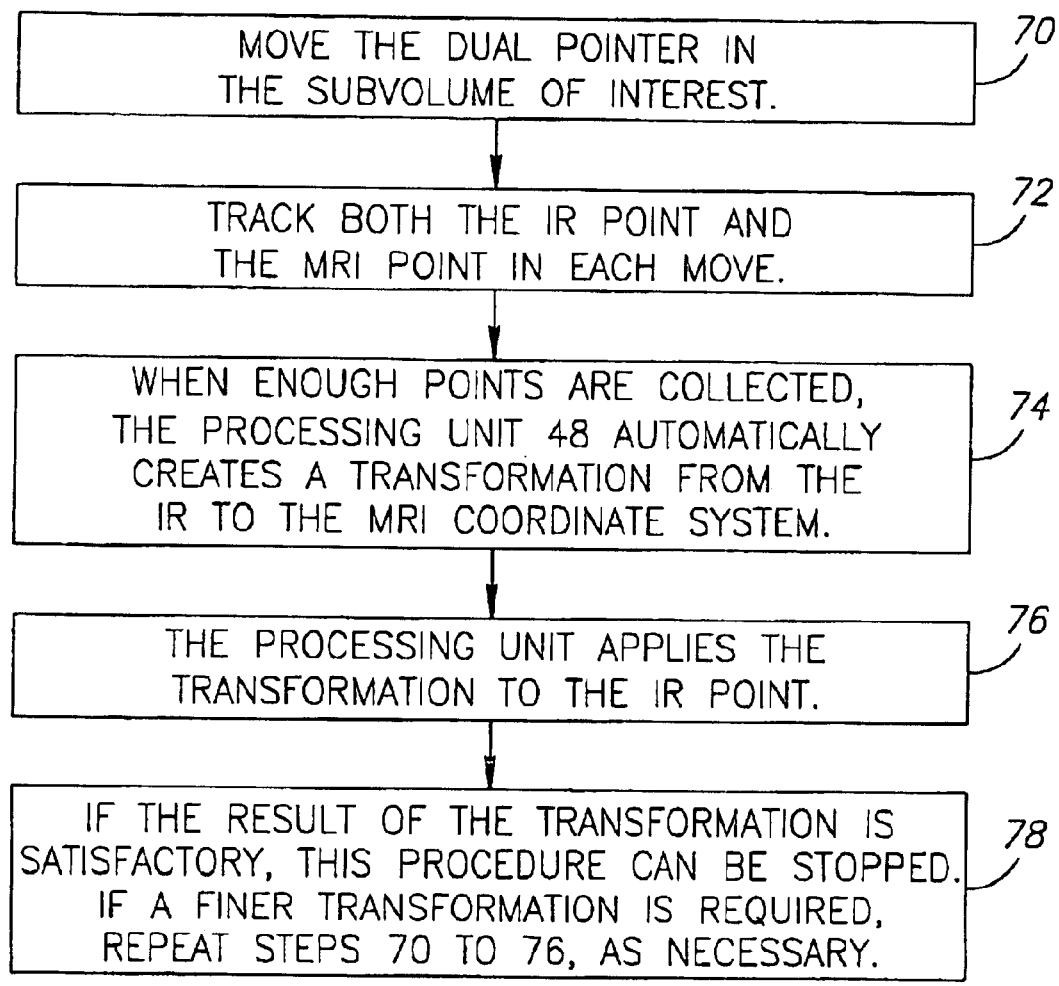
FIG. 4 is a chart of the procedure for performing local transformation of the IR point to the MRI point of a dual pointer in accordance with a preferred embodiment of the present invention.

At any time, it is possible to perform local transformation of the IR point to the MRI point as shown in the flowchart of FIG. 4 and in the following list:

70. Move the dual pointer in the subvolume of interest.

72 Track both the IR point and the MRI point in each move.

74 When enough points are collected, the processing unit 48 automatically creates a transformation from the IR to the MRI coordinate system.

76 The processing unit applies the transformation to the IR point.

78 If the result of the transformation is satisfactory, this procedure can be stopped. If a finer transformation is required, repeat steps 70 to 76, as necessary.

The local transformation procedure is particularly useful for overcoming mapping error due the non-Euclidean geometry of the image or changes in environmental factors such as temperature changes or movement of ferromagnetic devices.

Figure 5:
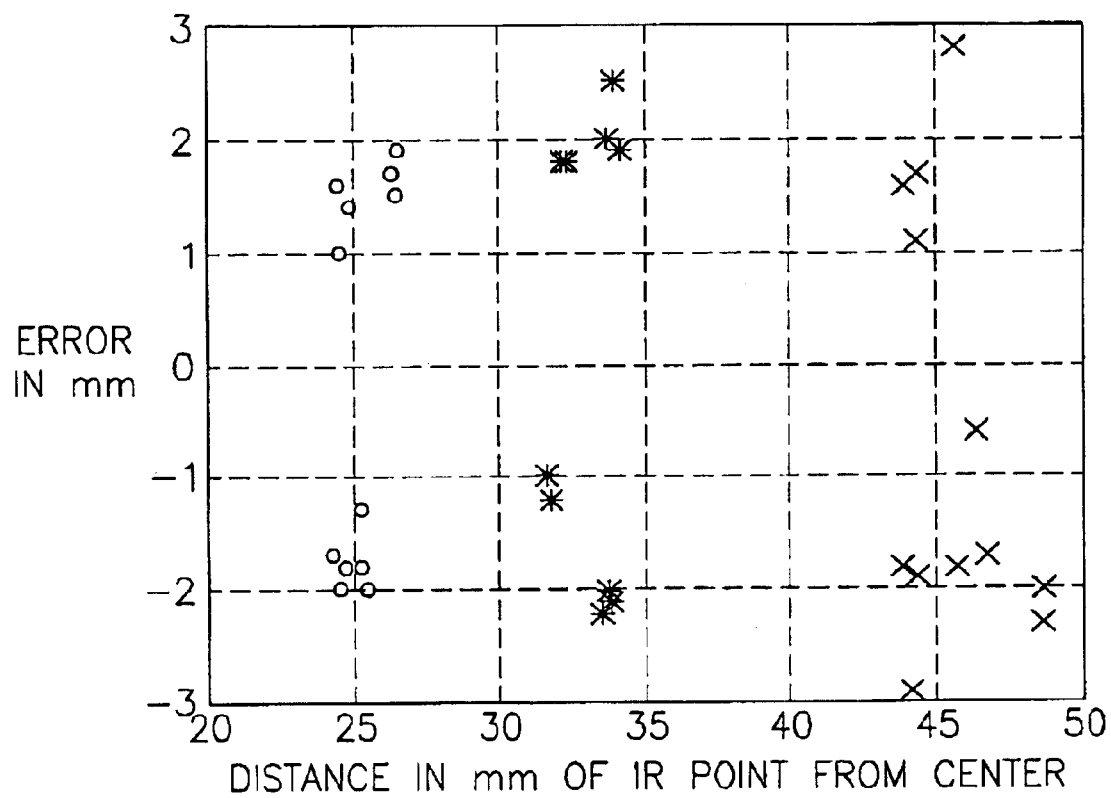
FIG. 5 is a graph of errors in mapping the IR point to the MRI point. This problem is overcome by the present invention.

The mapping error is illustrated in FIG. 5, where the X axis is the distance from center of image and the Y axis is the magnitude of the mapping error.

FIG. 5 shows that as the dual pointer moves away from the center of the magnet, both the error of the mapping of the IR point to the MRI point and the spread of that error increase due to the non-Euclidean nature of the MRI image. The figure shows that the magnitude and the spread of error increases towards the boundary of the image.

The local transformation procedure can also be used for the initial transformation described earlier in this specification. In that case, the local transformation is performed in the subvolume at the center of the magnets.

Local transformation can also be used to correct a loss of registration, such as can occur if there is untracked movement of the component holding the object being scanned or of the magnet.

Furthermore, once the local transformation is good enough, the IR point can be confidently used alone (i.e., where the MRI point is not tracked, such as when the MRI device is moved).

In addition to the uses of the IR point described above, the positions of the IR reflectors themselves can also be used as references in combination with the MRI point for several purposes.

Figure 6:
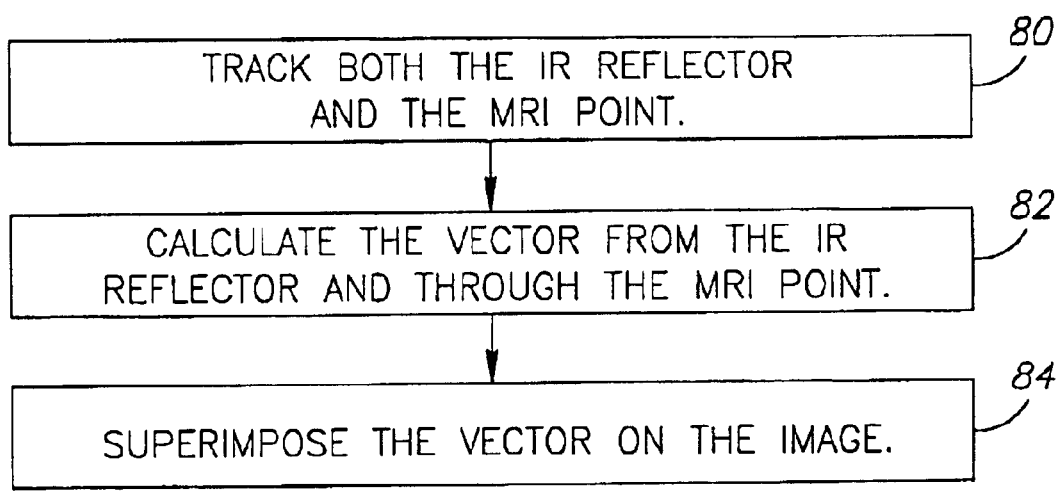
FIG. 6 shows the procedure steps for projecting a vector with a margin of error that is smaller than the discretization using a dual pointer in accordance with a preferred embodiment of the present invention.

One such use is to enable projection of a vector with a margin of error that is smaller than the discretization (image resolution). The procedure is as shown in the flowchart of FIG. 6 and in the following list:

80. Track both the IR reflector and the MRI point.
82. Calculate the vector from the IR reflector and through the MRI point.
84. Superimpose the vector on the image.

Figure 7:
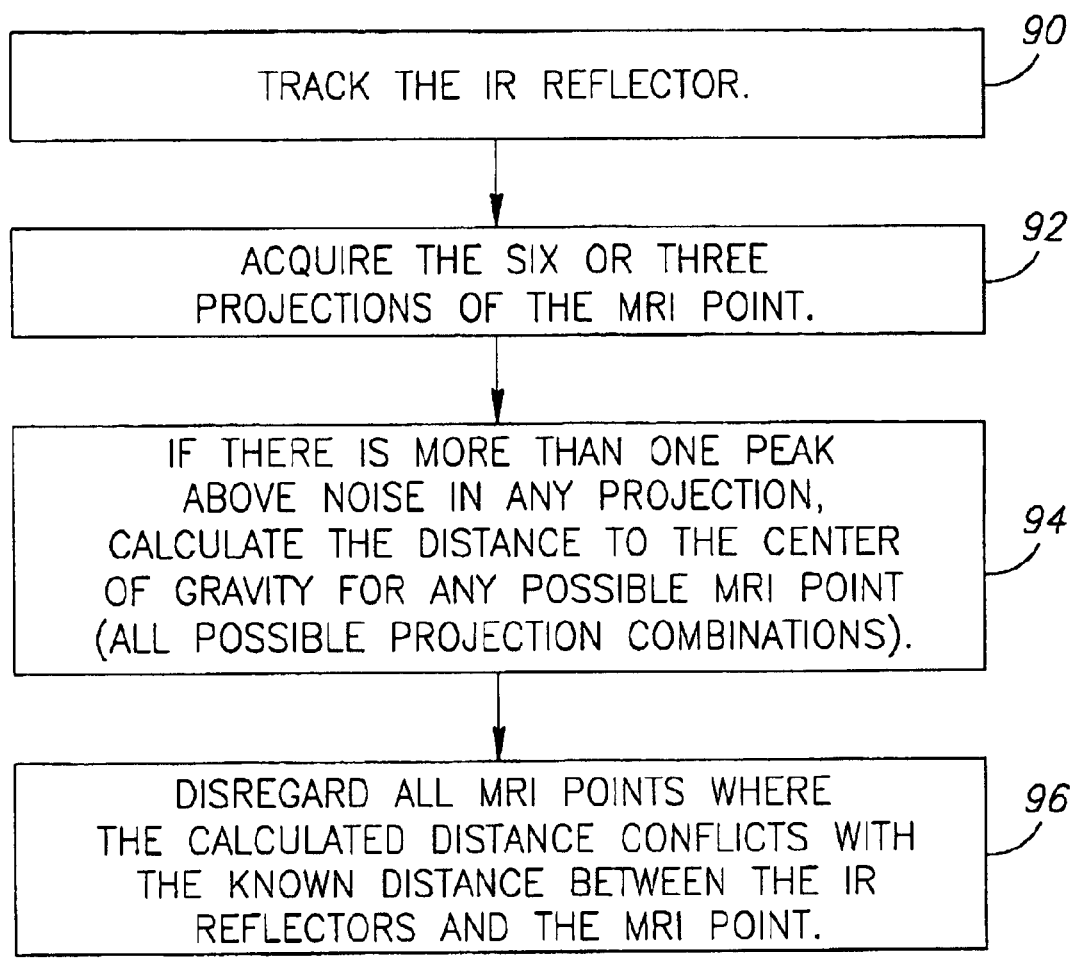
FIG. 7 shows the procedure steps automatically filtering false peaks caused by RF interference, including time-dependent interference, using a dual pointer in accordance with a preferred embodiment of the present invention.

Another use of the IR reflectors with the MRI point is to automatically filter false peaks caused by RF interference, including time-dependent interference. The procedure is as shown in the flowchart of FIG. 7 and in the following list:

90. Track the IR reflector.
92. Acquire the six projections of the MRI point. Using six projections, the position in the absolute coordinate system of the MRI sample can be calculated.
94. If there is more than one peak above noise in any projection, calculate the distance to the center of gravity for any possible MRI point (all possible projection combinations).
96. Disregard all MRI points where the calculated distance conflicts with the known distance between the IR reflectors and the MRI point.

Figure 8:
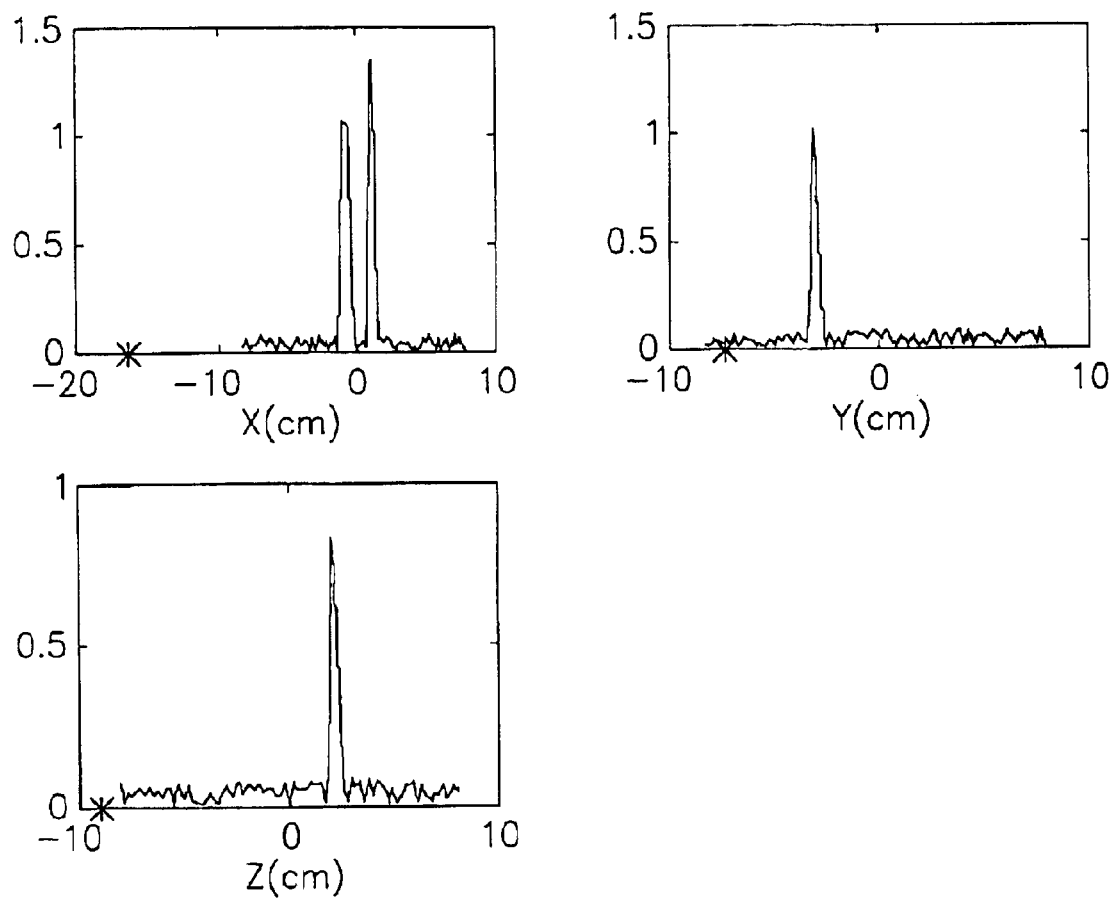
FIG. 8 is a set of graphs of MRI projections in which there is a false peak on one of the projections due to electromagnetic interference. This problem is overcome by the present invention.

FIG. 8 is an example of MRI projections where there is a false peak on the X projection. A procedure for determining the correct peak in this case would be as follows:

$xir = -1.6390e+001$ (Distance in cm of the IR point from the center of the magnet in the X direction)

$yir = -7.3322e+000$ (Distance in cm of the IR point from the center of the magnet in the Y direction)

$zir = -9.0838e+000$ (Distance in cm of the IR point from the center of the magnet in the Z direction)

$xw1 = -1.1520e-001$ (Center of gravity of the first peak (MRI point) in the X projection)

$xw2 = 2.0133e-001$ (Center of gravity of the second peak (MRI point) in the X projection)

$yw1 = -3.5733e-001$ (Center of gravity of the first peak (MRI point) in the Y projection)

$zw1 = 2.1600e-001$ (Center of gravity of the first peak (MRI point) in the Z projection)

wand_length1=sqrt((xir−xw1)^2+(yir−yw1) ^2+(zir−zw1) ^2)

wand_length2=sqrt((xir−xw2) ^2+(yir−yw1) ^2+(zir−zw1) ^2)

If wand_length1=known distance, disregard xw2, otherwise disregard xw1.

It is noted that while the embodiments shown in the accompanying drawings employ IR radiation for tracking IR reflective elements on the dual pointer in absolute coordinates, this may be performed using other tracking methods, such as an AC (alternating current) or electromagnetic (RF, visible light, microwaves etc.) system.

It is also noted that while the embodiments shown in the accompanying drawings employ magnetic resonance for the scanning of the image and of magnetic resonance responsive elements on the dual pointer, this may be performed using other scanning devices, such as employing an ESR (electron spin resonance) system or a gradient tracing system, with elements responsive to that imaging device used for the purpose ascribed here to the magnetic resonance responsive elements on the dual pointer.

Similarly, one skilled in the art could implement the absolute coordinate tracking of the dual pointer using another type of absolute position tracking system, such as electromagnetic radiation in other ranges (RF, visible light, microwaves, etc.) or AC (alternating current) marking.

In both cases such an invention would still remain within the scope of the present invention as defined by the appended Claims.

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

What is claimed is:

1. A method for enabling accurate positioning and tracking of an object relative to that object's coordinates in physical space and its coordinates in an image of the object, comprising:

providing a tracking means;

providing a magnetic resonance imaging means;

providing a dual pointing means comprising marking means detectable by said tracking means and magnetic resonance responsive means;

providing a processing means;

pointing with said dual pointing means in the imaging volume of the magnetic resonance imaging means;

tracking the location of said marking means, calculating the direction and tip location of said dual pointing means, based on said tracking by said tracking means;

acquiring an image with said magnetic resonance imaging means;

applying the same projection sequence used to acquire said image to obtain three projections of the magnetic responsive means;

processing said projections to calculate the direction of the dual pointing device and the location of its tip—based on said magnetic responsive means;

calculating the magnitude of the mapping error between the location of the dual pointing means' tip according to said tracking means and its location according magnetic resonance responsive means;

calculating a local transformation for the mapping error;

repeating the above to obtain mapping errors for a number of points, whereby paid local transformations can be applied to accurately map the coordinates of said dual pointing device in physical space as tracked by said tracking means to its coordinates in the image as calculated from the magnetic responsive means.

2. The method of claim 1, further comprising displaying the mapping error as well as the location and direction of the dual pointing means, as determined from the tracking means and as determined from the magnetic resonance responsive means, in the image.

3. The method of claim 2, wherein said magnetic resonance imaging means is an interventional magnetic resonance imaging means.

4. A method for projection a vector into an image captured by a magnetic resonance imaging means, comprising:

providing a tracking means;

providing a magnetic resonance imaging means providing a dual pointing means comprising marking means detectable by said tracking means and magnetic resonance responsive means;

providing a processing means;

pointing with said dual pointing means in the imaging volume of the magnetic resonance imaging means;

tracking the location of said marking means;

acquiring an image with said magnetic resonance imaging means;

applying the same projection sequence used to acquire said image to obtain three projections of said magnetic responsive means;

processing said three or six projections to calculate the location of the magnetic responsive means;

calculating the vector using as end points the location of the markers and the location of the magnetic resonance responsive means;

displaying the vector in the image, whereby a vector is projected into the image.

5. The method of claim 4 wherein the margin of error for the vector is smaller than the image discretization.

6. The method of claim 4, wherein said magnetic resonance imaging means is an interventional magnetic resonance imaging means.

7. A method for filtering out false peaks in the projection of a magnetic resonance signal acquired by a magnetic resonance imaging means, comprising:

providing a tracking means;

providing a magnetic resonance imaging means;

providing a dual pointing means comprising marking means detectable by said tracking means and magnetic resonance responsive means;

providing a processing means;

pointing with said dual pointing means in the imaging volume of the magnetic resonance imaging means;

tracking the location of said marking means;

acquiring an image with said magnetic resonance imaging means;

applying the same projection sequence used to acquire said image to obtain three projections of said magnetic responsive means;

calculating, where there is more than one peak above noise in any projection of the magnetic resonance responsive samples, the distance to the center of gravity, for each possible location of the tip of the dual pointing means indicated by the magnetic resonance responsive samples;

disregarding all locations where the calculated distance conflicts with the known distance between said markers and said magnetic resonance responsive means;

displaying the tip of the dual pointing means as indicated by the magnetic resonance responsive sample, whereby radio frequency interference is prevented from interfering with tracking the dual pointing means in the magnetic resonance image.

8. The method of claim 7, wherein said magnetic resonance imaging means is an interventional magnetic resonance imaging means.

9. A dual pointing device to be used in cooperation with an imaging apparatus, which is an electron spin resonance system, a tracking system, and an object to be imaged, the pointing device comprising:

a pointing member of a predetermined shape;

at least one sample of material responsive to the imaging apparatus, located on or inside said pointing member in a predetermined position and arranged, according to its composition, shape, or geometry, to register as a distinct point in an image acquired by the imaging apparatus;

at least one marker registerable on the tracking system, the marker located within said pointing member in a predetermined position and arranged, according to its geometry or other properties, so that the tracking system can determine information about the pointing member such as the location of the pointing member's tip and the pointing member's direction;

a processing means adapted to communicate with the tracking system and the imaging apparatus, to determine the relation between the coordinate set of the imaging apparatus and the coordinate set of the tracking means, and to translate the coordinates of said pointing member's tip as determined by the tracking system, from the absolute coordinate set of the tracking means to the coordinate set of the imaging apparatus and to superimpose it on the image, whereby the location of said pointing member's tip in the image coordinates and its location in the tracking system coordinates are superimposed in an image acquired by the imaging apparatus.

10. The device as claimed in claim 9, wherein the imaging apparatus is a gradient tracing system.

11. A dual pointing device to be used in cooperation with a magnetic resonance imaging apparatus, a tracking system, and an object to be imaged, the pointing device comprising:

a pointing member of a predetermined shape;

at least one of a plurality of magnetic resonance responsive samples geometrically arranged within said member to have a distinct directionality, located on or inside said pointing member in a predetermined position and arranged, according to its composition, shape, or geometry, to register as a distinct point in an image obtained by the magnetic resonance imaging apparatus;

at least one marker detectable by the tracking system, the marker located within said pointing member in a predetermined position and arranged, according to its geometry or other properties, so that the tracking system can determine information about the pointing member such as the location of the pointing member's tip and the pointing member's direction; and a processing means adapted to communicate with the tracking means and the magnetic resonance imaging apparatus, to determine the relation between the coordinate set of the magnetic resonance imaging apparatus and the coordinate set of the tracking means, and to translate the coordinates of said pointing member's tip as determined by the tracking system, from the absolute coordinate set of the tracking means to the coordinate set of the magnetic resonance imaging apparatus and to superimpose it on an image, whereby the location of said pointing member's tip in the image coordinates and its location in the tracking system coordinates are known.

12. A dual pointing device to be used in cooperation with a magnetic resonance imaging apparatus, a tracking system, and an object to be imaged, the pointing device comprising:

a pointing member of a predetermined shape;

at least one of a plurality of magnetic resonance responsive samples differentiated by MRI contrast, located on or inside said pointing member in a predetermined position and arranged, according to its composition, shape, or geometry, to register as a distinct point in an image obtained by the magnetic resonance imaging apparatus;

at least one marker detectable by the tracking system, the marker located within said pointing member in a predetermined position and arranged, according to its geometry or other properties, so that the tracking system can determine information about the pointing member such as the location of the pointing member's tip and the pointing member's direction; and a processing means adapted to communicate with the tracking means and the magnetic resonance imaging apparatus, to determine the relation between the coordinate set of the magnetic resonance imaging apparatus and the coordinate set of the tracking means, and to translate the coordinates of said pointing member's tip as determined by the tracking system, from the absolute coordinate set of the tracking means to the coordinate set of the magnetic resonance imaging apparatus and to superimpose it on an image, whereby the location of said pointing member's tip in the image coordinates and its location in the tracking system coordinates are known.

13. A dual pointing device to be used in cooperation with a magnetic resonance imaging apparatus, a tracking system, and an object to be imaged, the pointing device comprising:

a pointing member of a predetermined shape;

three magnetic resonance responsive samples, located on or inside said pointing member in a predetermined position and arranged, according to its composition, shape, or geometry, to register as a distinct point in an image obtained by the magnetic resonance imaging apparatus;

at least one marker detectable by the tracking system, the marker located within said pointing member in a predetermined position and arranged, according to its geometry or other properties, so that the tracking system can determine information about the pointing member such as the location of the pointing member's tip and the pointing member's direction; and a processing means adapted to communicate with the tracking means and the magnetic resonance imaging apparatus, to determine the relation between the coordinate set of the magnetic resonance imaging apparatus and the coordinate set of the tracking means, and to translate the coordinates of said pointing member's tip as determined by the tracking system, from the absolute coordinate set of the tracking means to the coordinate set of the magnetic resonance imaging apparatus and to superimpose it on an image, whereby the location of said pointing member's tip in the image coordinates and its location in the tracking system coordinates are known.

14. The device as claimed in claim 13, wherein said three magnetic resonance responsive samples are each provided in a shape of a disc.

15. The device as claimed in claim 13, wherein the gaps between said three magnetic resonance responsive samples are distinctly different whereby this aides in determining the directionality of said device.

16. A dual pointing device to be used in cooperation with a magnetic resonance imaging apparatus, a tracking system, and an object to be imaged, the pointing device comprising:

a pointing member of a predetermined shape;

at least one magnetic resonance responsive sample, located on or inside said pointing member in a predetermined position and arranged, according to its composition, shape, or geometry, to register as a distinct point in an image obtained by the magnetic resonance imaging apparatus;

at least one marker detectable by the tracking system, the marker geometrically arranged within said member to have a distinct directionality, located within said pointing member in a predetermined position and arranged, according to its geometry or other properties, so that the tracking system can determine information about the pointing member such as the location of the pointing member's tip and the pointing member's direction; and a processing means adapted to communicate with the tracking means and the magnetic resonance imaging apparatus, to determine the relation between the coordinate set of the magnetic resonance imaging apparatus and the coordinate set of the tracking means, and to translate the coordinates of said pointing member's tip as determined by the tracking system, from the absolute coordinate set of the tracking means to the coordinate set of the magnetic resonance imaging apparatus and to superimpose it on an image, whereby the location of said pointing member's tip in the image coordinates and its location in the tracking system coordinates are known.

17. A dual pointing device to be used in cooperation with a magnetic resonance imaging apparatus, a tracking system, and an object to be imaged, the pointing device comprising:

a pointing member of a predetermined shape;

at least one magnetic resonance responsive sample, located on or inside said pointing member in a predetermined position and arranged, according to its composition, shape, or geometry, to register as a distinct point in an image obtained by the magnetic resonance imaging apparatus;

at least one marker detectable by the tracking system, the marker geometrically arranged within said member to have a distinct rotational angle, located within said pointing member in a predetermined position and arranged, according to its geometry or other properties, so that the tracking system can determine information about the pointing member such as the location of the pointing member's tip and the pointing member's direction; and a processing means adapted to communicate with the tracking means and the magnetic resonance imaging apparatus, to determine the relation between the coordinate set of the magnetic resonance imaging apparatus and the coordinate set of the tracking means, and to translate the coordinates of said pointing member's tip as determined by the tracking system, from the absolute coordinate set of the tracking means to the coordinate set of the magnetic resonance imaging apparatus and to superimpose it on an image, whereby the location of said pointing member's tip in the image coordinates and its location in the tracking system coordinates are known.

18. A dual pointing device to be used in cooperation with a magnetic resonance imaging apparatus, a tracking system, and an object to be imaged, the pointing device comprising:

a pointing member of a predetermined shape;

three magnetic resonance responsive samples, located on or inside said pointing member in a predetermined position and arranged, according to its composition, shape, or geometry, to register as a distinct point in an image obtained by the magnetic resonance imaging apparatus;

at least one marker detectable by the tracking system, the marker located within said pointing member in a predetermined position and arranged, according to its geometry or other properties, so that the tracking system can determine information about the pointing member such as the location of the pointing member's tip and the pointing member's direction; and a processing means adapted to communicate with the tracking means and the magnetic resonance imaging apparatus, to determine the relation between the coordinate set of the magnetic resonance imaging apparatus and the coordinate set of the tracking means, and to translate the coordinates of said pointing member's tip as determined by the tracking system, from the absolute coordinate set of the tracking means to the coordinate set of the magnetic resonance imaging apparatus and to superimpose it on an image, whereby the location of said pointing member's tip in the image coordinates and its location in the tracking system coordinates are known.

19. A method for enabling accurate positioning and tracking of an object relative to that object's coordinates in physical space and its coordinates in an image of the object, comprising:

providing a tracking means;

providing a magnetic resonance imaging means;

providing a dual pointing means comprising marking means detectable by said tracking means and magnetic resonance responsive means;

providing a processing means;

pointing with said dual pointing means in the imaging volume of the magnetic resonance imaging means;

tracking the location of said marking means;

calculating the direction and tip location of said dual pointing means, based on said tracking by said tracking means;

acquiring an image with said magnetic resonance imaging means, applying the same projection sequence used to acquire said image to obtain three projections of the magnetic responsive means;

processing said projections to calculate the direction of the dual pointing device and the location of its tip based on said magnetic responsive means;

calculating the magnitude of the mapping error between the location of the dual pointing means's tip according to said tracking means and its location according magnetic resonance responsive means;

calculating a local transformation for the mapping error;

repeating the above to obtain mapping errors for a number of points, whereby, said local transformations can be applied to accurately map the coordinates of said dual pointing device in physical space as tracked by said tracking means to its coordinates in the image as calculated from the magnetic responsive means.

20. The method of claim 19, further comprising displaying the mapping error as well as the location and direction of the dual pointing means, as determined from the tracking means and as determined from the magnetic resonance responsive means, in the image.

21. The method of claim 19, wherein said magnetic resonance imaging means is an interventional magnetic resonance imaging means.

22. A method for projecting a vector into an image captured by a magnetic resonance imaging means, comprising:

providing a tracking means;

providing a magnetic resonance imaging means;

providing a dual pointing means comprising marking means detectable by said tracking means and magnetic resonance responsive means;

providing a processing means;

pointing with said dual pointing means in the imaging volume of the magnetic resonance imaging means;

tracking the location of said marking means;

acquiring an image with said magnetic resonance imaging means;

applying the same projection sequence used to acquire said image to obtain three projections of said magnetic responsive means;

processing said three or six projections to calculate the location of the magnetic responsive means;

calculating the vector using as end points the location of the markers and the location of the magnetic resonance responsive means; and displaying the vector in the image, whereby a vector is projected into the image.

23. The method of claim 22, wherein the margin of error for the vector is smaller than the image discretization.

24. The method of claim 22, wherein said magnetic resonance imaging means is an interventional magnetic resonance imaging means.

25. A method for filtering out false peaks in the projections of a magnetic resonance signal acquired by a magnetic resonance imaging means, comprising:

providing a tracking means;

providing a magnetic resonance imaging means;

providing a dual pointing means comprising marking means detectable by said tracking means and magnetic resonance responsive means;

providing a processing means;

pointing with said dual pointing means in the imaging volume of the magnetic resonance imaging means;

tracking the location of said marking means;

acquiring an image with said magnetic resonance imaging means;

applying the same projection sequence used to acquire said image to obtain three projections of said magnetic responsive means;

calculating, where there is more than one peak above noise in any projection of the magnetic resonance responsive samples, the distance to the center of gravity, for each possible location of the tip of the dual pointing means indicated by the magnetic resonance responsive samples;

disregarding all locations where the calculated distance conflicts with the known distance between said markers and said magnetic resonance responsive means; and displaying the tip of the dual pointing means as indicated by the remaining location indicated by the magnetic resonance responsive sample, whereby radio frequency interference is prevented from interfering with tracking the dual pointing means in the magnetic resonance image.

* * * * *